United States Patent [19]

Benoit et al.

[11] Patent Number: 5,068,229

[45] Date of Patent: Nov. 26, 1991

[54] INSECTICIDAL METHOD

[75] Inventors: Marc Benoit, Roquevaire; Jean-Pierre Demoute, Auriol, both of France

[73] Assignee: Roussel Uclaf, Paris, France

[21] Appl. No.: 557,186

[22] Filed: Jul. 23, 1990

[51] Int. Cl.$^5$ ............................................. A01N 57/00
[52] U.S. Cl. ........................................................ 514/114
[58] Field of Search ................................................ 514/114

[56] References Cited

U.S. PATENT DOCUMENTS 4,264,532  4/1981  Tsuruoka et al. ...................... 562/11

Primary Examiner—Allen J. Robinson
Attorney, Agent, or Firm—Bierman and Muserlian

[57] ABSTRACT

A method of combatting insects comprising contacting the insects with an insecticidally effective amount of at least one member of the group consisting of glufosinate of the formula

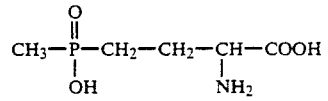

and its salts.

9 Claims, No Drawings

INSECTICIDAL METHOD

STATE OF THE ART

Glufosinate or DL-(homoalanin-4-yl)-methyl phosphine acid is a well known, commercially available product described in the Pesticide Manual, a World Compendium, 7th Edition, page 302 published by the British Crop Protection Council. Its ammonium salt is the active herbicidal ingredient in BASTA, a commercial herbicide. Other pertinent art includes U.S. Pat. No. 4,264,532 and Chemical Patents Index Basic Abstracts Journal, B 38, No. 68819 of Nov. 14, 1979.

OBJECTS OF THE INVENTION

It is an object of the invention to provide a novel method of combatting insects.

This and other objects and advantages of the invention will become obvious from the following detailed description.

THE INVENTION

The novel method of the invention of combatting insects comprises contacting the insects with an insecticidally effective amount of at least one member of the group consisting of glufosinate of the formula

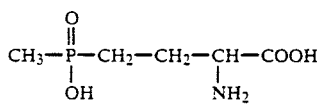   I and its salts. Examples of suitable salts are the ammonium salt and alkali metal salts such as sodium and potassium with the ammonium salt being preferred.

Among the compositions of the invention are those containing an insecticidally effective amount of an aqueous solution containing glufosinate and/or one of its salts and a propyleneglycol ether, or one or more fluorinated acids, or an alkaline salt of lauryl ether sulfate. Preferred compositions contain two or more of the following constituents: a propyleneglycol ether, a fluorinated acid and an alkaline salt of lauryl ether sulfate. Especially preferred is a composition containing as the active ingredient an effective amount of the commercial form BASTA.

The amount of the active ingredient is usually less than 200 g/l preferably not more than 20 g/l, more preferably not more than 10 g/l such as 1 g/l or less.

The compositions may be in the form of powders, granules, suspensions, emulsions, solutions, aerosol solutions, combustible strips, baits or other preparations normally employed for the use of such compounds. In addition to the active ingredient, the compositions may contain a non-ionic surface-active vehicle and/or agent to ensure an uniform dispersion of the components of the mixture. The vehicle used can be a liquid such as water, alcohol, hydrocarbons or other organic solvents, a mineral, animal or vegetable oil.

Particularly interesting results have been obtained by incorporating the active ingredient or ingredients with watering or in alimentary compositions called baits for example compositions characterized in that they contain from 0.5 to 15 mg of glufosinate for 1 g/l bait.

The method of the invention is useful against all types of parasitic insects of vegetation, premises or animals. They can be used for combatting insects in the agricultural domain, for example, aphids, the larvae of lepidopter and coleoptera and for combatting parasites of animals such as lice.

The results obtained in various biological tests summarized hereafter in the experimental part clearly show that the method of the invention is effective in combatting a large variety of insects at all stages of their development and particularly certain strains resistant to pyrethrinoids. It is particularly useful for combatting insects in premises, for example cockroaches such as Germanic cockroaches, for combatting ants or also for combatting flies and mosquitoes.

In the following examples there are described several preferred embodiments to illustrate the nvention. However, it should be understood that the invention is no intended to be limited to the specific embodiments.

EXAMPLE 1

An aqueous solution of glufosinate at 10 g/l was prepared and 1 ml of this solution was incorporated into 1 g of rodent's biscuit used to feed Germanic cockroaches. The cockroaches died progressively from the fourth day.

EXAMPLE 2

An aqueous solution of glufosinate at 10 g/l was prepared and this solution was given as watering water to Germanic cockroaches. Mortality was total after 5 days.

EXAMPLE 3

An aqueous solution of glufosinate at 1 g/l was prepared and this solution was sprayed on haricot-bean leaves used to feed third-stage larvae of *Spodoptera littoralis* and a total mortality of the larvae was obtained. When larvae of *Spodoptera littoralis* resistant to pyrethrinoids were exposed to the same conditions, a total morality of the larvae was also obtained.

EXAMPLE 4

An aqueous solution of glufosinate at 1 g/l was prepared and this solution was sprayed on broad-bean leaves used to feed first-stage larvae of *Aphis craccivora* and a total mortality of the larvae was obtained.

EXAMPLE 5

An artificial medium was prepared containing 70 ppm of glufosinate and it was placed over the eggs of *Anthonomus grandis*. No adults appeared.

Various modifications of the method may be made without departing from the spirit or scope thereof and it should be understood that the invention is to be limited only as defined in the appended claims.

What we claimed is:

1. A method of combatting insects comprising contacting the insects with an insecticidally effective amount of at least one member of the group consisting of glufosinate of the formula

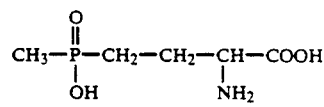   I and its salts.

2. The method of claim wherein the active ingredient is the ammonium salt of glufosinate.

3. The method of claim 1 wherein the active ingredient is in an aqueous solution containing a propyleneglycol ether.

4. The method of claim 1 wherein the active ingredient is in an aqueous solution containing at least one fluorinated acid.

5. The method of claim wherein the active ingredient is in an aqueous solution containing an alkali metal salt of lauryl ether sulfate.

6. The method of claim 1 wherein the active ingredient is in an aqueous solution containing at least two members of the group consisting of propyleneglycol ether, a fluorinated acid and an alkali metal salt of lauryl ether sulfate.

7. The method of claim 1 wherein the active ingredient is incorporated in an alimentary bait composition.

8. The method of claim 1 wherein the insects are cockroaches.

9. The method of claim 1 wherein the insects are ants.

* * * * *